United States Patent [19]

Wilk

[11] Patent Number: 5,297,536
[45] Date of Patent: Mar. 29, 1994

[54] METHOD FOR USE IN INTRA-ABDOMINAL SURGERY

[76] Inventor: Peter J. Wilk, 185 W. End Ave., New York, N.Y. 10023

[21] Appl. No.: 934,914

[22] Filed: Aug. 25, 1992

[51] Int. Cl.⁵ ............................................. A61B 1/00
[52] U.S. Cl. .................... 128/4; 128/898; 606/140
[58] Field of Search ............. 128/4, 8, 898, 6; 606/213, 139, 140, 144, 151, 46, 1; 604/54

[56] References Cited

U.S. PATENT DOCUMENTS

| | | |
|---|---|---|
| 3,643,653 | 2/1972 | Takahashi et al. ............... 128/6 |
| 3,760,810 | 9/1973 | Van Hoorn ...................... 606/140 |
| 4,103,680 | 8/1978 | Yoon .................................. 128/6 |
| 4,471,766 | 9/1984 | Terayama .......................... 128/6 |
| 4,735,194 | 4/1988 | Stiegmann ......................... 128/6 |
| 4,976,717 | 12/1990 | Boyle ............................... 606/119 |
| 5,224,497 | 7/1993 | Ehlers ............................... 128/898 |

Primary Examiner—Richard J. Apley
Assistant Examiner—Karen A. Jalbert
Attorney, Agent, or Firm—R. Neil Sudol; Henry D. Coleman

[57] ABSTRACT

A method for use in intra-abdominal surgery comprises the steps of inserting a tubular member into a natural body cavity of a patient through a natural body opening, manipulating the tubular member from outside the patient so that a distal end of the tubular member engages a wall of the natural body cavity, and forming a fluid tight connection between the distal end of the tubular member and the wall. Additional steps of the method include inserting an incising instrument through the tubular member upon insufflation of the abdominal cavity, manipulating the incising instrument from outside the patient to form a perforation through the surface of the wall, and moving a distal end of an endoscope through the tubular member and through the perforation. The endoscope is used to visually inspect internal body tissues in an abdominal cavity of the patient. Subsequently, a surgical operation is executed on the internal body tissues of the patient by manipulating an endoscopic surgical instrument passed along the endoscope through the natural body opening, the natural body cavity and the perforation into the abdominal cavity. After the intra-abdominal operation, the surgical instrument and the endoscope are withdrawn from the abdominal cavity through the perforation, the perforation is closed, and the endoscope and the tubular member are withdrawn from the natural body cavity.

17 Claims, 3 Drawing Sheets

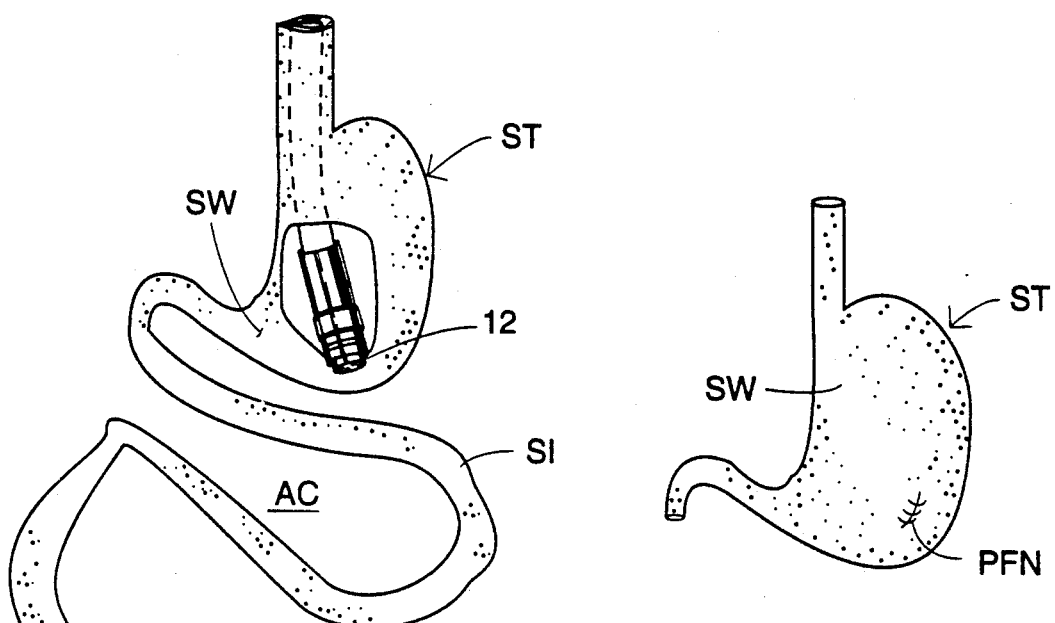
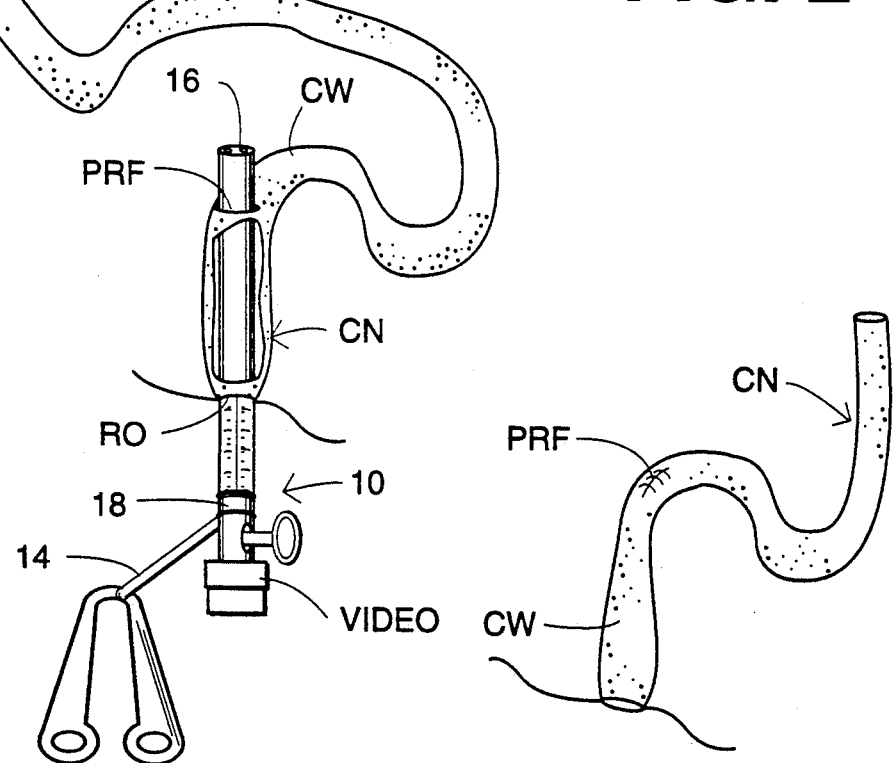
FIG. 1
FIG. 2
FIG. 3

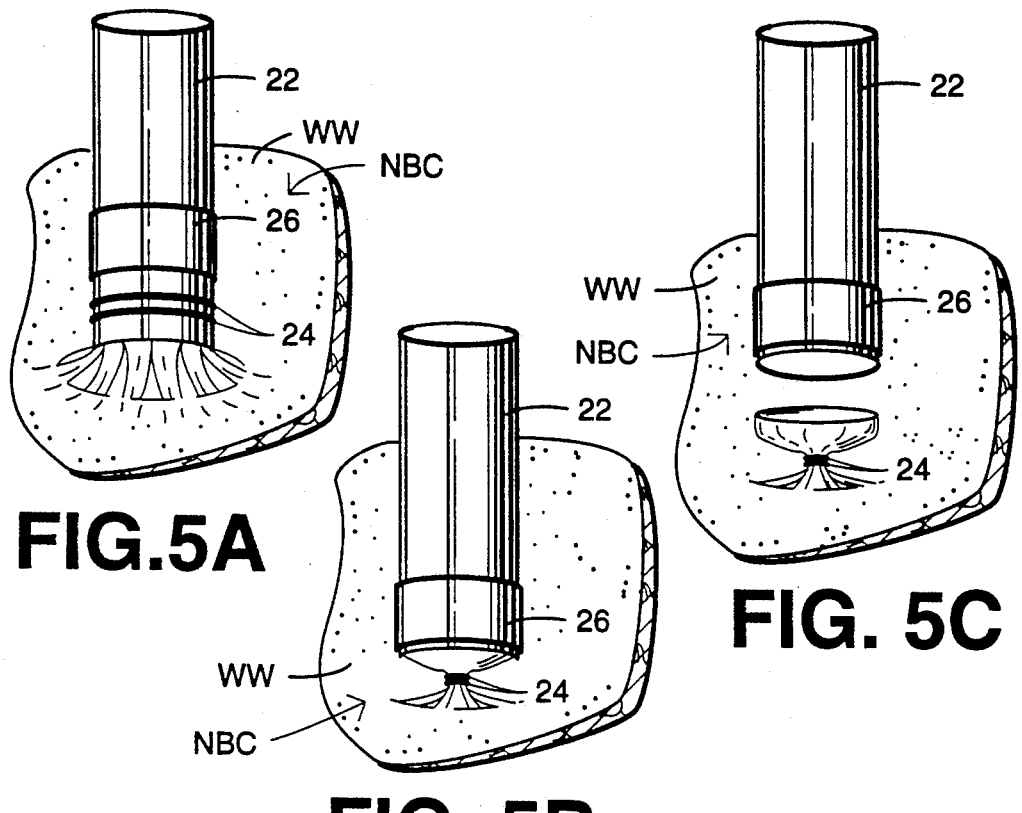
FIG. 5A
FIG. 5B
FIG. 5C
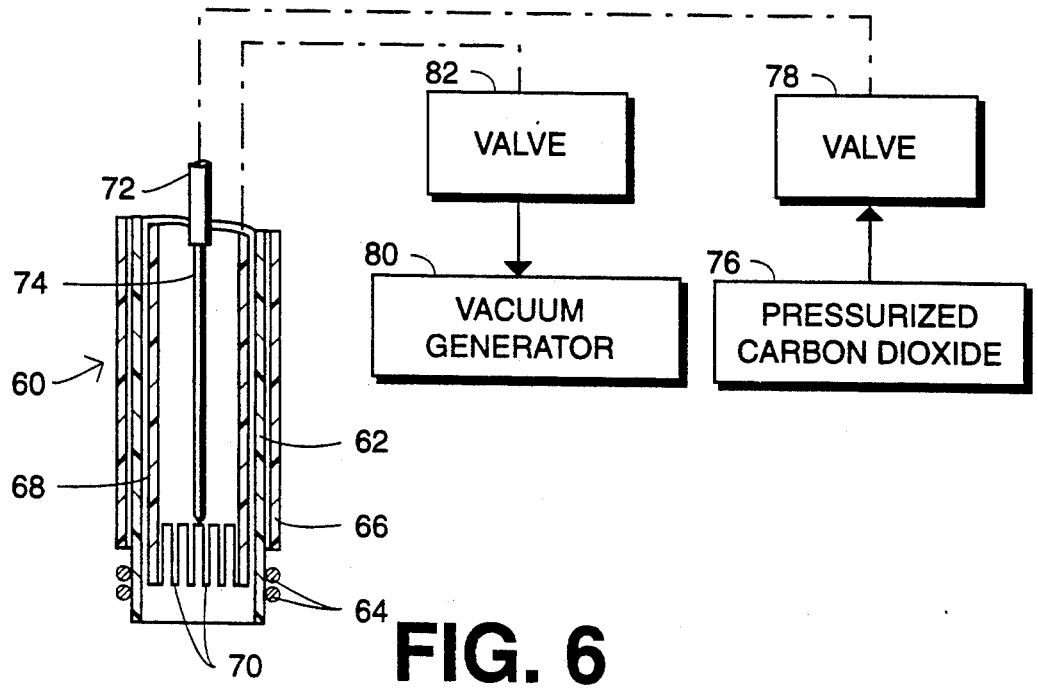
FIG. 6

METHOD FOR USE IN INTRA-ABDOMINAL SURGERY

BACKGROUND OF THE INVENTION

This invention relates to a method for use in intra-abdominal surgery.

Intra-abdominal surgery has been conventionally performed by forming an incision in the abdominal wall and operating on internal body organs through the incision This method of surgery invariably results in substantial blood loss, as well as extended pain to the patient after surgery has been completed.

The disadvantages of conventional intra-abdominal surgery has been subtantially reduced by the technique of laparoscopic surgery wherein access to abdominal organs is obtained through trocar sleeves or laparoscopic cannulas disposed in respective perforations formed in the abdominal wall of the patient by trocars. Hospital stays and patient trauma are reduced.

OBJECTS OF THE INVENTION

An object of the present invention is to provide a new method for the performance of intra-abdominal surgery.

Another object of the present invention is to provide such a method which reduces the incisions in the abdominal wall required during intra-abdominal surgery.

Another, more particular, object of the present invention is to provide an endoscopic method for obtaining access to abdominal organs.

These and other objects of the invention will be apparent from the descriptions and illustrations provided herein.

SUMMARY OF THE INVENTION

A method for use in intra-abdominal surgery comprises, in accordance with the present invention, the steps of (a) inserting an endoscope through a natural body opening into a natural body cavity or organ of a patient, (b) inserting an endoscopic type incising instrument into the natural body cavity along a passage established by the endoscope, (c) manipulating the incising instrument from outside the patient to form a perforation in an internal wall of the natural internal body cavity, (d) moving a distal end of the endoscope through the perforation, (e) using the endoscope to visually inspect internal body tissues in an abdominal cavity of the patient, (f) executing a surgical operation on the internal body tissues by manipulating an endoscopic surgical instrument passed along the endoscope through the natural body opening, the natural body cavity and the perforation into the abdominal cavity, (g) withdrawing the surgical instrument and the endoscope from the abdominal cavity through the perforation, (h) closing the perforation, and (i) withdrawing the endoscope from the natural body cavity.

Accordingly, in a method in accordance with the present invention, no incisions are performed in the abdominal wall of the patient. Access to the abdominal cavity is through a natural body opening such as the mouth, the anus, or a vaginal orifice, and a natural body cavity as the stomach, the colon or the vagina. The opening into the abdomen is closed subsequent to the surgery, thus preventing access to the abdomen through the perforation after surgery has been completed.

Pursuant to another feature of the present invention, the method further comprises the step of inserting an ancillary tube through the natural body opening and into the natural body cavity prior to the step of manipulating the incising instrument to form the perforation. The endoscope is inserted through the ancillary tube. The distal end of that tube is brought into fluid tight engagement with the internal wall of the natural body cavity prior to the manipulation of the incising instrument to form the perforation. The endoscope is thus inserted through the ancillary tube and the perforation.

According to another feature of the present invention, the method also comprises the steps of insufflating the abdominal cavity through the ancillary tube and the perforation prior to moving the distal end of the endoscope through the perforation.

According to an additional feature of the present invention, where the endoscope is provided with a sheath having an expandable channel, the incising instrument is inserted through the channel upon insertion of the endoscope through the natural body opening and into the natural body cavity. Also, the surgical instrument is inserted through the sheath channel prior to the step of executing.

A method for use in intra-abdominal surgery comprises, in accordance with another embodiment of the present invention, the steps of (i) inserting a tubular member into a natural body cavity of a patient through a natural body opening, (ii) manipulating the tubular member from outside the patient so that a distal end of the tubular member engages a wall of the natural body cavity, (iii) forming a fluid tight connection between the distal end of the tubular member and the wall, (iv) inserting a hollow needle through the tubular member and through a surface of the wall encircled by the distal end of the tubular member, and (v) insufflating the abdominal cavity by forcing pressurized gas through the needle and into the abdominal cavity. Additional steps of the method in accordance with this embodiment of the invention include (vi) inserting an incising instrument through the tubular member upon insufflation of the abdominal cavity, (vii) manipulating the incising instrument from outside the patient to form a perforation through the surface of the wall, (viii) moving a distal end of an endoscope through the tubular member and through the perforation, (ix) using the endoscope to visually inspect internal body tissues in an abdominal cavity of the patient, and (x) executing a surgical operation on the internal body tissues by manipulating an endoscopic surgical instrument passed along the endoscope through the natural body opening, the natural body cavity and the perforation into the abdominal cavity. Subsequent to the performance of the intra-abdominal operation, the surgical instrument and the endoscope are withdrawn from the abdominal cavity through the perforation, the perforation is closed, and the endoscope and the tubular member are withdrawn from the natural body cavity.

According to another feature of this embodiment of the present invention, the endoscope is inserted into the tubular member prior to the manipulation of the incising instrument, the incising instrument being inserted through a biopsy channel of the endoscope. The biopsy channel may be formed in a sheath removably attached to an insertion member of the endoscope.

As described above, the formation of the connection between the distal end of the tubular member and the wall of the natural body cavity is accomplished by applying suction to the wall via the tubular member, thereby drawing the wall partially into the distal end of the tubular member.

A method in accordance with the present invention reduces trauma to the individual even more than laparoscopic procedures. Hospital convalescence stays are even shorter.

BRIEF DESCRIPTION OF THE DRAWING

FIG. 1 is a diagram of the gastro-intestinal tract, showing two points of entry from the tract into the abdominal cavity in a surgical procedure accordance with the present invention.

FIG. 2 is a diagram of the stomach, showing closure of an entry point into the abdominal cavity upon completion of surgery in accordance with the present invention.

FIG. 3 is a diagram of the sigmoidal colon, showing closure of an entry point into the abdominal cavity upon completion of surgery in accordance with the present invention.

FIGS. 5A-5C are partially cross-sectional views of the stomach and partially side elevational views of the assembly of FIG. 4, showing successive steps in the use of the assembly in a method in accordance with the present invention.

FIG. 6 is partially a block diagram and partially a longitudinal cross-sectional view of a surgical assembly for use in a surgical method in accordance with the present invention.

DETAILED DESCRIPTION

Figure 4:
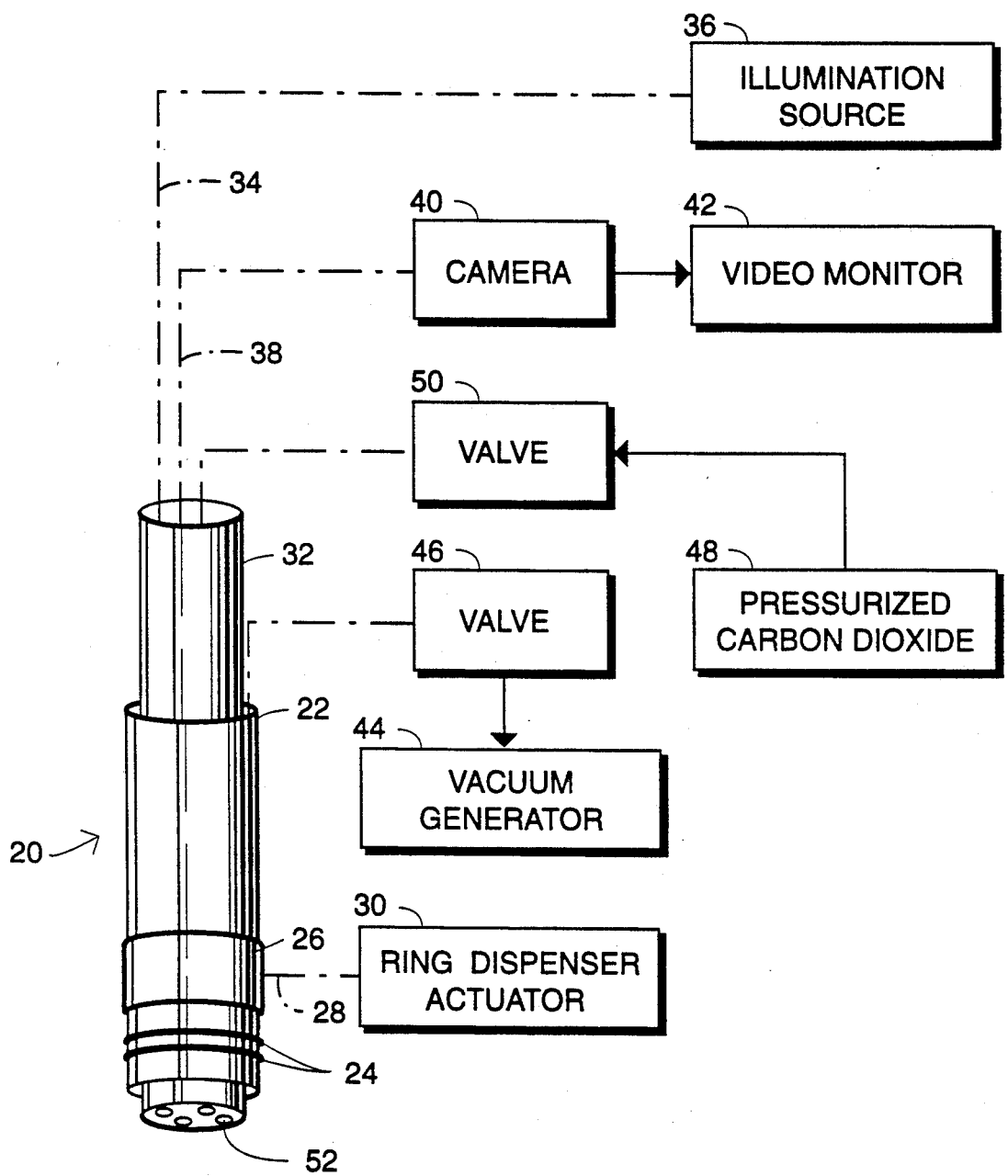
FIG. 4 is partially a block diagram and partially a schematic side perspective view of a surgical assembly for use in a surgical method in accordance with the present invention.

As illustrated in FIG. 1, intra-abdominal surgery is performed without the formation of an incision in the abdominal wall of the patient. Instead, endoscopic surgical instruments 10 or 12 are inserted into the patient through a natural body opening such as the anus or rectal orifice RO or the mouth (not illustrated) and through a wall CW or SW of a natural body cavity or organ such as the colon CN or the stomach ST. Intra-abdominal surgery can alternatively be performed on a female patient by inserting surgical instruments into the patient's abdominal cavity through the vagina and the wall of the cul-de-sac.

In performing surgery though the colon, for example, endoscope 10 is inserted through rectal orifice RO into the sigmoidal section of the colon CN and used to visually inspect the internal surfaces thereof for purposes of determining a suitable point of entry. An endoscopic type incising instrument 14 is inserted into the colon CN along a passage established by the endoscope, for example, through a biopsy channel 16 of the insertion member 18 of endoscope 10 or through an ancillary channel in an endoscopic sheath (not shown). Such a sheath with collapsed biopsy channels is disclosed in U.S. Pat. Nos. 4,646,722 and 5,025,778 to Silverstein et al. the disclosure of which is hereby incorporated by reference herein.

Incising instrument 14 is manipulated from outside the patient to form a perforation PRF in wall CW of the sigmoidal portion of colon CN. Subsequently, a distal end of endoscope insertion member 18 is inserted through perforation PRF, the endoscope being used then to visually inspect internal body tissues, e.g., small intestine SI, colon CN, etc., in the abdominal cavity AC of the patient. Upon locating a surgical site, a surgical operation is executed on the internal body tissues by manipulating an endoscopic surgical instrument (e.g., incising instrument 14) passed along endoscope insertion member 18 through rectal orifice RO, colon CN and perforation PRF.

A surgical operation performable in abdominal cavity may include, for example, a colecystectomy, a ressection of the colon, repair of traumatized organs, etc. Many operations which can presently be executed via laparoscopic techniques may be performed endoscopically through a perforation formed in a natural body cavity or organ such as the stomach ST, the colon CN or the vagina.

Such endoscopic surgery will be facilitated by endoscopic instruments (graspers, forceps, scalpels, staplers, suturing devices, irrigators, cauterization devices, etc.) having flexible distal ends which are steerable via cables extending along the lengths of the instruments from respective control knobs at the proximal ends of the instruments. This steering enables greater control of the surgical instruments.

Upon completion of the intra-abdominal surgery, the endoscopic surgical instrument(s) (e.g., 14) and endoscope 10 are withdrawn from the abdominal cavity AC through perforation PRF. Perforation PRF is then closed and endoscope 10 is withdrawn from colon CN. FIG. 3 shows the colon CN with perforation PRF closed upon completion of the surgery. FIG. 2 shows closure of a perforation PFN formed in stomach ST during intra-abdominal surgery through the stomach ST as described above and hereinafter.

As illustrated in FIG. 4, an endoscopic assembly 20 for use in performing intra-abdominal surgery through a natural body cavity comprises an outer tube 22 provided at a distal end with a pair of 0 rings 24 and a sleeve 26 for sliding 0 rings 24 off the distal end of tube 22 at the termination of an intra-abdominal surgical procedure. Sleeve 26 is connected via a link 28 such as a rod or pair of rods to an actuator 30 disposed at the proximal end of the instrument assembly 20.

Endoscopic instrument assembly 20 further comprises an endoscopic insertion member 32 having a fiber optic illumination guide 34 connected to a light source 36 and a fiber optic image guide 38 connected to a video camera 40 (e.g., a charge coupled device). Camera 40 is in turn coupled to a video monitor 42 for enabling visual inspection of an image carried by guide 38. A vacuum generator 44 is connected to tube 22 via a valve 46, while a pressurized source 48 of a gas such as carbon dioxide communicates via a valve 50 with a biopsy channel 52 of endoscopic insertion member 32.

As illustrated in FIG. 5A, prior to the incising of a wall WW of a natural body cavity or organ NBC, a distal end of tube 22 is brought into engagement with the wall. Suction is applied to the wall WW by opening valve 46 to connect vacuum generator 44 to tube 22.

Tube 22 and endoscopic insertion member 32 may be inserted together through a natural body opening into an organ, endoscopic insertion member 32 being manipulated to facilitate visual inspection of the internal tissues of the patient via monitor 42. Upon selection of a suitable entry site, endoscopic insertion member 32 is withdrawn at least partially from tube 22 to facilitate the formation of a negative-pressure connection between the distal end of tube 22 and the wall of the organ.

Pressurized carbon dioxide source 48 may be connected to a tubular instrument (not shown) slidably inserted into biopsy channel 52 of endoscopic insertion member 32, the tubular instrument being formed at a distal end with a needle (not shown) for piercing the wall WW of the organ. Upon a piercing of the wall and an entry of the needle into the abdominal cavity, valve 50 is actuated to connect source 48 to the tubular member for a time long enough to insufflate the abdominal cavity.

After a suitable expansion of the abdomen has been attained, the insufflation needle and tubular member are withdrawn from biopsy channel 52 and replaced with an endoscopic incising instrument as described hereinabove with reference to instrument 14 of FIG. 1. The incising instrument is manipulated from outside the patient to form a perforation in the wall WW of the natural cavity or organ.

Upon the completion of an intra-abdominal operation, executed via instruments inserted through biopsy channel 52 and other biopsy channels of endoscopic insertion member 32, and upon the withdrawal of such instruments and endoscopic insertion member 32 from the abdominal cavity, actuator 30 is operated to slide sleeve 26 in a distal direction over the endoscopic insertion member, thereby sliding O rings 24 onto wall WW, as illustrated in FIG. 5B. Rings 24 serve to clamp the tissues of wall WW, thereby closing the perforation through which an operation has been performed. As shown in FIG. 5C, upon the disposition of rings 24, vacuum generator 44 is disconnected from tube 22 and the distal end of the tube is disengaged from wall WW. Endoscopic insertion member 32 may be used at that juncture to inspect the closure. Subsequently, insertion member 32 and tube 22 are removed from the patient.

As illustrated in FIG. 6, another instrument assembly 60 for use in performing intra-abdominal surgery via a natural body opening and an associated internal organ of the patient comprises a first tubular member 62 provided at a distal end with a pair of elastic O rings 64 A dispensing tube 66 slidably coaxial with and surrounding tube 62 is provided for pushing rings 64 off of tubular member 62 at the termination of an operation. An auxiliary tubular member 68 inserted inside tubular member 62 is formed at a distal end with a plurality of longitudinally extending prongs or barbs 70.

FIG. 6 additionally shows a hollow rod 72 provided at a distal end with a hollow needle 74. Rod 72 communicates with a source 76 of pressurized carbon dioxide via a valve 78. A vacuum generator or suction source 80 is connected to tubular member 62 via a valve 82.

Instrument assembly 60 may be used in a manner similar to the procedure described hereinabove with reference to FIGS. 4 and 5A–5C. Upon the locating of a suitable abdominal entry site in a wall of an internal organ, with or without the use of an endoscope, tubular member 62 is pushed in a distal direction so that the distal end of the tubular member is brought into engagement with the wall of the organ. Valve 82 is then operated to connect suction source 80 to tubular member 62, thereby sucking the wall of the organ into the distal end of tubular member 62. Inner tubular member 68 is then pushed in a distal direction so that prongs 70 are at least partially embedded in the tissues of the organ wall.

If an endoscope has been inserted through inner tubular member 68 to aid in the location of an entry point, the endoscope may be removed prior to the insertion of rod 72 and needle 74. Alternatively, as discussed above, rod 72 and needle 74 may be inserted through a biopsy channel of the endoscope. Needle 74 is used to insufflate the abdominal cavity and is withdrawn. The remainder of the procedure is clear.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A method for use in intra-abdominal surgery, comprising the steps of:
   inserting an endoscope through a natural body opening into a natural body cavity of a patient;
   inserting an endoscopic type incising instrument into said natural body cavity along a passage established by said endoscope;
   manipulating said incising instrument from outside the patient to form a perforation in an internal wall of said natural internal body cavity;
   moving a distal end of said endoscope through said perforation;
   using said endoscope to visually inspect internal body tissues in an abdominal cavity of the patient;
   executing a surgical operation on said internal body tissues by manipulating an endoscopic surgical instrument passed along said endoscope through said natural body opening, said natural body cavity and said perforation into said abdominal cavity;
   withdrawing said surgical instrument and said endoscope from said abdominal cavity through said perforation;
   closing said perforation; and
   withdrawing said endoscope from said natural body cavity.

2. The method defined in claim 1, further comprising the step of inserting an ancillary tube through said natural body opening and into said natural body cavity prior to said step of manipulating said incising instrument to form said perforation, said endoscope being inserted through said ancillary tube.

3. The device defined in claim 2, further comprising the step of forming a fluid tight engagement between a distal end of said ancillary tube and said internal wall of said natural body cavity prior to said step of manipulating said incising instrument to form said perforation, said endoscope being inserted through said ancillary tube and said perforation.

4. The method defined in claim 3, further comprising the step of insufflating said abdominal cavity through said ancillary tube and said perforation prior to said step of moving.

5. The method defined in claim 1, further comprising the step of insufflating said abdominal cavity through said ancillary tube and said perforation prior to said step of moving.

6. The method defined in claim 1 wherein said natural body opening is the mouth and said natural body cavity is the stomach.

7. The method defined in claim 1 wherein said natural body opening is the anus and said natural body cavity is the colon.

8. The method defined in claim 1 wherein said natural body opening is the vaginal orifice and said natural body cavity is the vagina canal.

9. The method defined in claim 1 wherein said endoscope is provided with a sheath having an expandable channel, said incising instrument being inserted through said channel upon insertion of said endoscope through said natural body opening and into said natural body cavity.

10. The method defined in claim 1 wherein said endoscope is provided with a sheath having an expandable channel, said surgical instrument being inserted through said channel prior to said step of executing.

11. A method for use in intra-abdominal surgery, comprising the steps of:
    inserting a tubular member into a natural body cavity of a patient through a natural body opening;
    manipulating said tubular member from outside the patient so that a distal end of said tubular member engages a wall of said natural body cavity;
    forming a fluid tight connection between said distal end of said tubular member and said wall;
    inserting a hollow needle through said tubular member and through a surface of said wall encircled by said distal end of said tubular member;
    insufflating the abdominal cavity by forcing pressurized gas through said needle and into the abdominal cavity;
    upon insufflation of the abdominal cavity, inserting an incising instrument through said tubular member;
    manipulating said incising instrument from outside the patient to form a perforation through said surface of said wall;
    moving a distal end of an endoscope through said tubular member and through said perforation;
    using said endoscope to visually inspect internal body tissues in an abdominal cavity of the patient;
    executing a surgical operation on said internal body tissues by manipulating an endoscopic surgical instrument passed along said endoscope through said natural body opening, said natural body cavity and said perforation into said abdominal cavity;
    withdrawing said surgical instrument and said endoscope from said abdominal cavity through said perforation;
    closing said perforation; and
    withdrawing said endoscope and said tubular member from said natural body cavity.

12. The method defined in claim 11 wherein said endoscope is inserted into said tubular member prior to said step of manipulating said incising instrument, said incising instrument being inserted through a biopsy channel of said endoscope.

13. The method defined in claim 12 wherein said biopsy channel is formed in a sheath removably attached to an insertion member of said endoscope.

14. The method defined in claim 11 wherein said step of forming includes the step of applying suction to said wall via said tubular member, thereby drawing said wall partially into said distal end of said tubular member.

15. The method defined in claim 11 wherein said natural body opening is the mouth and said natural body cavity is the stomach.

16. The method defined in claim 11 wherein said natural body opening is the anus and said natural body cavity is the colon.

17. The method defined in claim 11 wherein said natural body opening is the vaginal orifice and said natural body cavity is the vagina canal.

* * * * *